United States Patent [19]

SaBell

[11] Patent Number: Plant 6,192

[45] Date of Patent: May 31, 1988

[54] BIRCH TREE

[75] Inventor: Wallace H. SaBell, Lakewood, Colo.

[73] Assignee: J. Frank Schmidt & Son Co., Boring, Oreg.

[21] Appl. No.: 689,812

[22] Filed: Jan. 8, 1985

[51] Int. Cl.[4] ..... A01H 5/00

[52] U.S. Cl. ..... Plt./51

[58] Field of Search ..... Plt./51

*Primary Examiner*—Robert E. Bagwill

*Attorney, Agent, or Firm*—Klarquist, Sparkman, Campbell, Leigh & Whinston

[57] ABSTRACT

A novel birch tree is described, characterized by white bark, a pyramidal shaped crown, strong upwardly arching branches angled at approximately 45° from the trunk, resistance to Winter die-back in Rocky Mountain climates, and large foliage.

1 Drawing Sheet

The present invention relates to a new and distinct variety of birch trees of the species botanically known as *Betula occidentalis* (Hooker). I have named my new variety "Rocky Mountain Splendor".

Some time ago, I purchased a group of hybrid birch seedling trees which were allegedly the result of a cross of the variety Water or Mountain Birch (*Betula occidentalis*, Hooker), with the variety European White Birch (*Betula pendula*, Roth). While observing this group of trees, which were being grown in a cultivated area of my nursery in Lakewood, Colo., my attention was attracted to one of these trees because it appeared to combine some of the best features of the European Birch tree with certain desirable characteristics of the Mountain Birch tree.

More specifically, the parent Rocky Mountain Splendor tree and progeny thereof subsequently asexually propagated under my direction by budding on European Birch understock, have been closely observed. As a result of these observations, I am convinced that my new tree represents a new and improved variety of birch tree as particularly evidenced by the following unique combination of characteristics, which have proven firmly fixed, are outstanding therein, and which distinguish it from other varieties of this species of which I am aware:

1. Mature trees with white bark;
2. A pyramidal shaped crown with strong branches consistently angled at about 45° from the trunk;
3. Resistance to Winter die-back of branches during the Winter in states such as Colorado;
4. Large foliage; and
5. Rapid growth.

The accompanying photographs depict the color of the foliage of my new variety as nearly true as is reasonably possible to make the same in a color illustration of this character.

FIG. 1 is a color photograph of a tree of the present invention taken after it's leaves have fallen to show the white bark of the tree;

FIG. 2 is a color photograph of an immature tree of my new variety, showing the large foliage and upright branches of the tree;

FIG. 3 is a color photograph of a leaf of a tree of my new variety in its Summer color, depicted with two leaves from a European White Birch tree to show the contrast in size; and FIG. 4 is a color photograph of a leaf of a tree of my invention, showing its yellow Autumn color.

One of the primary distinguishing features of my new tree is that at approximately age three, the bark of my new Rocky Mountain Splendor Birch tree develops a white color comparable to the white color of the European White Birch. In contrast, the bark of Mountain Birch trees is reddish brown to bronze and in some cases a cream-tan color, but not white. In addition, the crown of my new variety of birch tree assumes a generally pyramidal shape, with the tree having strong branches which are consistently angled at about 45° from the trunk. This characteristic enables my new variety to resist damage from heavy, wet snow which falls from time to time in the Rocky Mountain region. Also, the upright branching pattern of my new tree is dense, which makes it suitable for use in small settings. Although the Mountain Birch branches tend to be more upright than those of the European White Birch, each of these two trees branch in more of an irregular pattern than my new variety in that these trees typically have branches angling from upright to horizontal from the trunk. Furthermore, the European White Birch tree exhibits somewhat of a drooping or a weeping growth habit, making this tree more susceptible to damage by heavy snow. Also, my new variety exhibits a hardiness and resistance to Winter die-back which is comparable to the Mountain Birch variety. In comparison, the tips of European White Birch branches are susceptible to damage during harsh freezing weather.

In a pronounced difference from either of the parent trees, the foliage of my Rocky Mountain Splendor variety is typically twice as large as the foliage of either of the two parent trees. As a specific example, leaves of one-year old Rocky Mountain Splendor trees and one-year old European White Birch trees, growing in similar conditions in a nursery in Oregon, were compared. The leaves of the Rocky Mountain Splendor variety averaged 13.0 cm long and 9.9 cm wide. In contrast, the European White Birch leaves averaged 6.5 cm long and 5.1 cm wide. This comparison was made in October of 1983 from measurements of the fifth leaf down from the top of twenty trees of each variety. In addition, a comparison of a limited sampling of leaves from my Rocky Mountain Splendor variety with those of the Mountain Birch variety, the trees being grown in Colorado, was also made. The Rocky Mountain Splendor leaves which averaged 7.5 cm long and 5.0 cm wide, while Mountain Birch leaves averaged 3.4 cm long and 2.5 cm wide. This difference in leaf size gives my new variety of tree a distinct ornamental appearance.

My new variety of Rocky Mountain Splendor Birch also appears to grow faster than the European White Birch tree, although somewhat slower than the growth rate of Mountain Birch trees.

Other differences between my Rocky Mountain Splendor variety and the European White and Mountain Birch varieties of birch trees have also been observed. That is, the leaf of my variety has a slightly cordate base, an acute tip, margin with somewhat small rounded serrations, and is glabrous underneath, except for glandular dots found on the leaf veins. In comparison, the leaves of European White Birch trees have a truncate base, acuminate leaf tip, course sharp serrated leaf margin, and an underside which is glabrous. Also, the Mountain Birch tree leaves have a base which is cuneate to truncate, a tip which is acute to acuminate, a margin with sharp often double serrations, and which is glabrous except for glandular dots located throughout the underside of the leaf. Furthermore, the buds of my tree, like those of the Mountain Birch tree, are resinous. In contrast, the buds of European White Birch trees are not resinous. Also, the tips of the young twigs of my tree tend to be pubescent while those of the European White Birch tree are glabrous. In comparison, the tips of twigs of the Mountain Birch trees vary from glabrous to moderately pubescent.

Finally, like the Mountain Birch tree, my new variety seems more resistant to Birch Leaf Miner and rust than is the European White Birch tree.

Otherwise, so far as I have observed at this time, my new variety appears to be generally typical of the species.

The following is a detailed description of my new variety of Rocky Mountain Splendor Birch tree, with color terminology in accordance with The Royal Horticultural Society Color Chart (hereinafter RHS), published by The Royal Horticultural Society of London.

Parentage:

*Pollen Parent.*—*Betula occidentalis* (Hooker); synonymously known as *Betula fontinalis* (Sargent).

*Seed Parent.*—*Betula pendula* (Roth).

Classification:

*Botanical.*—Betula 'Rocky Mountain Splendor'.

Propagation: Holds to distinguishing characteristics through succeeding propagation by budding on European Birch understock.

Localities where grown and observed: Lakewood, Colo. and Boring, Oreg.

Tree: Overall upright, healthy, very vigorous; rapid growing.

*Crown.*—Generally pyramidal shape.

*Branches.*—Strong arching branches consistently angling approximately 45° from the trunk. Tips of young twigs slightly pubescent.

*Bark.*—Thin, cream-white color, readily peeling.

Hardiness: Hardy, resistant to winter die-back; resistant to Birch Leaf Miner and Rust.

Foliage:

*Leaves.*—Alternate, simple.

*Leaf size.*—Length—varies with location where grown, typically 5–14 cm long and 4–10 cm wide.

*Shape.*—Ovate.

*Margin.*—Serrated, teeth somewhat rounded, with margin approaching or becoming entire near the base.

*Tip.*—Acute.

*Base.*—Slightly cordate.

*Surface.*—Glabrous, except for glandular dots on the veins of the underside at the leaf.

*Color.*—Leaf Summer color is a parsley green color (similar to RHS 139A). In the Fall, the leaves turn to an Indian yellow color (similar to RHS 17C).

Buds: Resinous, sticky. Winter buds covered with greenish-brown imbricate scales.

Flowers: Male and female in separate catkins on the same tree. Male flowers in slender catkins typically 5–7 cm long, produced at or near the tips of the branchlets.

Fruits: Hanging or spreading cone-like structures typically 5–6 cm long consisting of numerous three lobed scales, each scale enclosing a tiny winged seed.

I claim:

1. A new and distinct variety of birch tree, substantially as herein shown and described, characterized particularly as to novelty by white bark, a pyramidal shaped crown, strong arching upright branches, resistance to Winter die-back and large foliage.

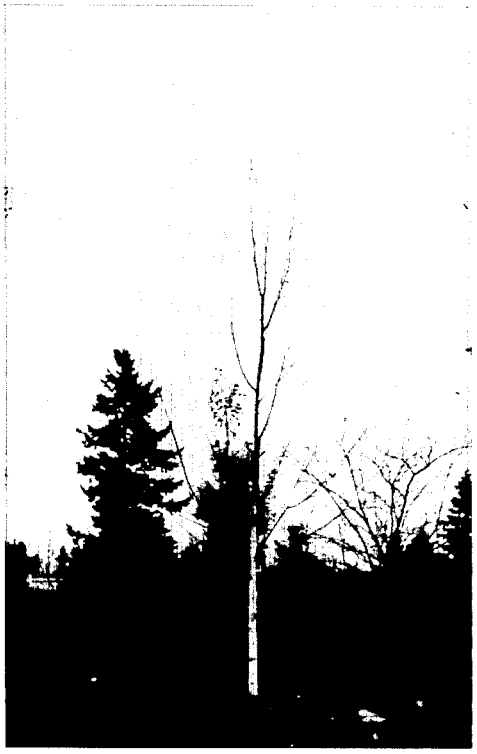
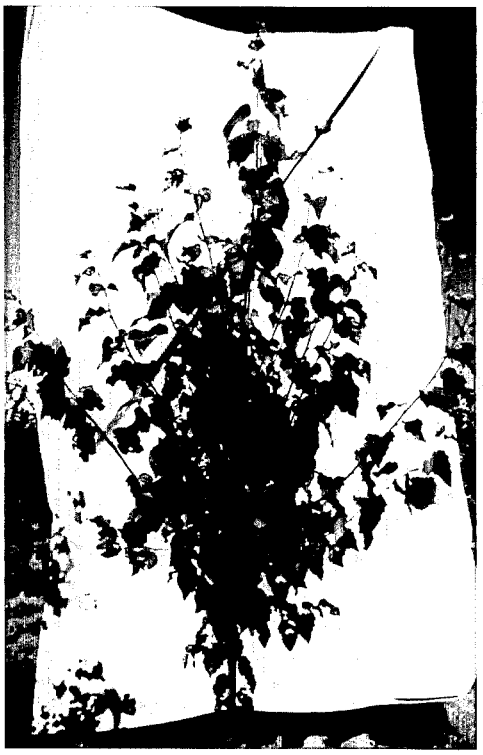
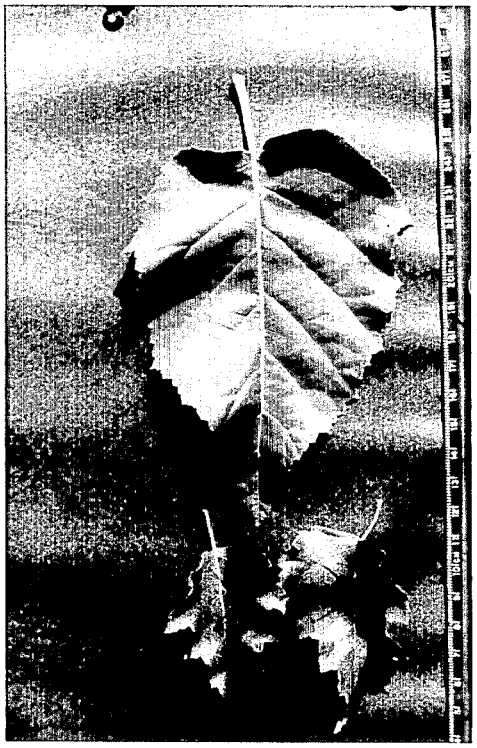
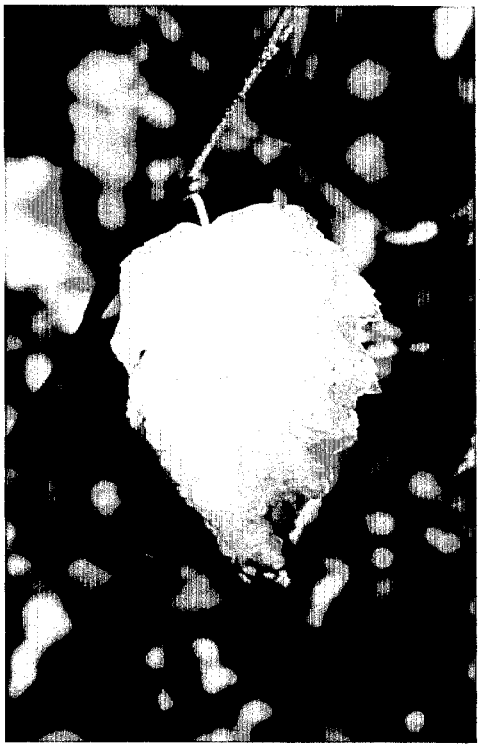

* * * * *